(12) United States Patent
Werblud

(10) Patent No.: US 6,302,234 B1
(45) Date of Patent: Oct. 16, 2001

(54) ACOUSTICALLY INSULATED FLEXIBLE TUBE ASSEMBLY FOR STETHOSCOPES

(76) Inventor: Marc S. Werblud, 9426 NE. 139th St., Kirrland, WA (US) 98034

( * ) Notice: Subject to any disclaimer, the term of this patent is extended or adjusted under 35 U.S.C. 154(b) by 0 days.

(21) Appl. No.: 09/531,022

(22) Filed: Mar. 18, 2000

(51) Int. Cl.[7] .................................................. A61B 7/02
(52) U.S. Cl. ........................................... 181/131; 138/131
(58) Field of Search .................... 181/131, 137; 381/67; 138/30, 131

(56) References Cited

U.S. PATENT DOCUMENTS

| | | | |
|---|---|---|---|
| 3,568,722 | * | 3/1971 | Runshe ..................... 138/30 |
| 5,713,412 | * | 2/1998 | Wepfer et al. ............ 138/30 |
| 5,883,340 | * | 3/1999 | Shieh ....................... 181/131 |
| 5,952,618 | * | 9/1999 | Deslauriers .............. 181/131 |

* cited by examiner

Primary Examiner—Khanh Dang
(74) Attorney, Agent, or Firm—Robert W. Jenny

(57) ABSTRACT

The tube assembly is made up of an outer, elastomeric tube, a close wound metal spring inside the outer tube and a layer of material inside the spring to provide a smooth inner surface for the assembly. The layer may be a thin-walled elastomeric plastic tube or a layer of elastomeric material applied to the inside of the spring. Also, the spring wire may be coated with elastomeric plastic.

6 Claims, 1 Drawing Sheet

ACOUSTICALLY INSULATED FLEXIBLE TUBE ASSEMBLY FOR STETHOSCOPES

BACKGROUND OF THE INVENTION

1. Field

The subject invention is in the field of tubular apparatus used for conducting acoustical energy which can be converted to sound by ears, apparatus such as ear horns and the tubular communications systems formerly used on ships. In particular it is in the field of such apparatus as applied to stethoscopes, i.e. the flexible tube connecting the chest piece which picks up the acoustic energy to the ear pieces which are inserted in a user's ears. Most particularly it is in the field of such tubes which are assemblies and include a feature or features which insulate the interior, energy transmitting portion of the tube from (1) extraneous ambient acoustic energy sources such as physical contact on the exterior of the tube assembly, finger contacts being one example, and (2) sounds generated in the ambient area of the use of the stethoscope.

2. Prior Art

The most pertinent prior art in this most particular field and known to the inventor of the subject invention is U.S. Pat. No. 5,952,618, issued to Deslauries. This patent covers a stethoscope, part of which is a conduit assembly comprising a flexible outer tube made of a material having a first density and at least one inner tube made of a material having a second density which is greater than the first density. The first tube is made of an elastomer such as a polymer or neoprene and the second tube is made of metal, preferably steel and is a close wound spring so that the conduit assembly is flexible and tends to be self straightening and kink free. The purpose of this construction is to acoustically insulate the assembly. The attenuation of acoustic energy transmitted through the wall of the assembly is attributed to the difference in the densities of the materials. The inventor of the subject invention believes that (1) the attenuation in lower frequency ranges is based on mechanical/structural support of the elastic outer tube by the stiff inner tube, and (2) that attenuation in higher frequency ranges is based on the inherent internal damping characteristics of the assembly and that the internal damping is based on conversion of acoustic energy to heat by the minute frictional actions between the inner and outer tubes. The inventor of the subject invention further believes that the essentially corrugated inner surface of the inner tube has negative effects on the transmission of acoustic energy through the assembly and that the acoustic attenuation achieved in this prior art assembly can be improved. Accordingly, the objectives of the subject invention are to provide, for use on stethoscopes, an acoustically insulated flexible tube having a smooth interior and optimized acoustical insulation.

SUMMARY OF THE INVENTION

The subject invention is an acoustically insulated flexible tube assembly for use on stethoscopes. The assembly comprises an elastomeric outer tube and an inner tube which fits snugly in the outer tube and is a close wound spring, preferably made of steel. The assembly further comprises a smooth plastic inner surface of the inner tube, the preferred plastic being Teflon®. This inner surface can be the inner surface of a third tube made of Teflon® or the wire of the spring may be coated with Teflon®. The invention is described in more detail below with reference to the attached drawings.

DETAILED DESCRIPTION OF THE INVENTION

Figure 1:
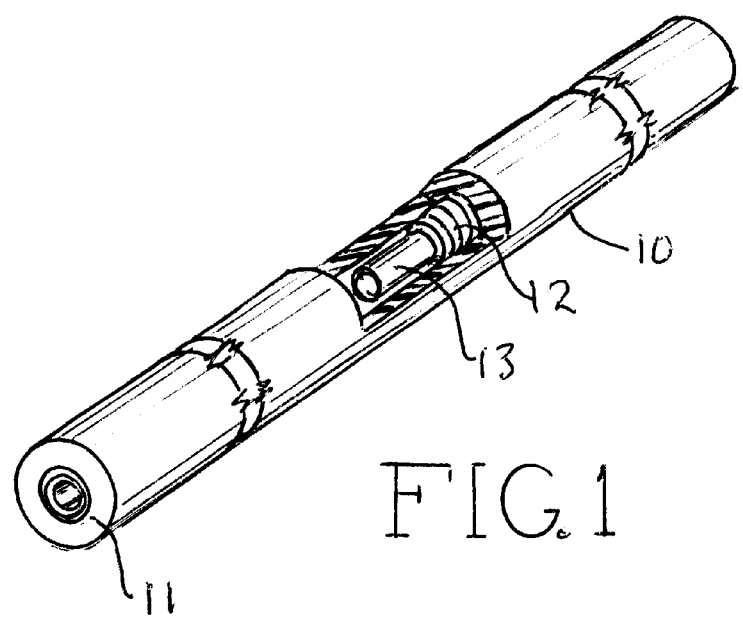
FIG. 1 is a cut-away sectional view of a preferred embodiment of the subject invention.

The subject invention is an acoustically insulated flexible tube assembly for use on stethoscopes. FIG. 1 is a cut-away sectional view of a preferred embodiment of the tube assembly 10. It comprises outer tube 11, made of elastomeric material such as neoprene, a first inner member 12 which is a close wound metal spring, wound to be preset in tension and a second, inner tube 13. Tube 13 may be made to fit snugly inside member 12 or it may be held in place by an elastomeric adhesive such as RTV Silicone Adhesive Sealant made by LOCTITE®. Alternately, the wire of the spring may be plastic coated.

Figure 2:
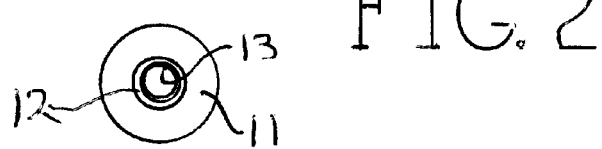
FIG. 2 is a section taken at 2—2 in FIG. 1.

FIG. 2 is a section taken at 2—2 in FIG. 1 with parts numbered as in FIG. 1. In various embodiments of the invention the spring may fit loosely in the tube, fit snugly in the tube or the two may be adhesively attached with elastomeric adhesive such as silicone adhesive. The three materials used in the tube assembly have different densities.

Figure 3:
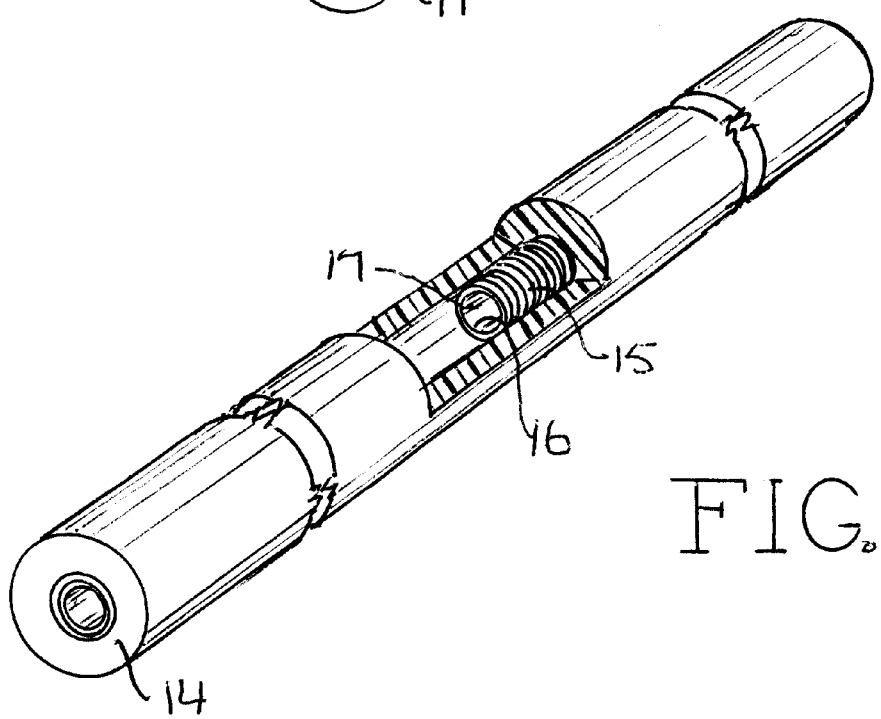
FIG. 3 is a cut-away sectional view of an alternate embodiment of the subject invention.

A second embodiment of the invention, shown in FIG. 3, comprises outer tube 14, close wound spring 15 fitting snugly in the outer tube and a layer 16 of silicone sealant applied to provide a smooth inner surface 17. The material which provides a smooth inner surface may be a coating on the spring wire, a layer of silicone sealant or a layer of the same material as that of the outer tube.

It is considered to be understandable from this description that the subject invention meets its objectives. It provides, for use on stethoscopes, an acoustically insulated flexible tube having a smooth interior and optimized acoustical insulation. The optimization results from the facts that (1) acoustic energy entering the tube assembly along its length must negotiate three materials having different densities, and (2) since the use of three materials presents more interfaces between materials than when two materials are used, there is more acoustic energy dissipation by the minute frictional actions in the interfaces.

It is also considered to be understood that while certain embodiments of the invention are disclosed herein, other embodiments and modifications of those disclosed are possible within the scope of the invention which is limited only by the attached claims.

I claim:

1. An acoustically insulated flexible tube assembly comprising:
    an elastomeric outer tube made of a first material,
    a close wound metallic spring made of spring wire, and
    material providing a smooth inner surface of said tube assembly,
    said close wound spring being inside and fitting snugly inside said outer tube, and
    said material for providing a smooth inner surface being inside said close wound spring.

2. The assembly of claim 1 in which said material for providing a smooth inner surface is a plastic coating on said spring wire.

3. The assembly of claim 1 in which said material for providing a smooth inner surface is an elastomeric tube.

4. The assembly of claim 1 in which said material for providing a smooth inner surface is elastomeric plastic applied inside said spring.

5. The assembly of claim 1 in which said material for providing a smooth inner surface is said first material.

6. The assembly of claim 3 further comprising elastomeric plastic adhesive between said elastomeric tube and said spring.

* * * * *